United States Patent [19]

Deinet et al.

[11] 4,373,953
[45] Feb. 15, 1983

[54] SURFACE-COATING COMPOSITIONS CONTAINING POLYVALENT METAL SALTS OF HYDROXYBENZOIC ACID ESTERS

[75] Inventors: Adolph J. Deinet, East Brunswick; William B. Woods, Lebanon, both of N.J.

[73] Assignee: Tenneco Chemicals, Inc., Piscataway, N.J.

[21] Appl. No.: 251,678

[22] Filed: Apr. 6, 1981

[51] Int. Cl.³ .............................................. C09D 5/14
[52] U.S. Cl. ........................................ 106/16; 106/17; 106/18; 106/18.32; 106/18.35; 106/18.36; 106/222; 106/263; 424/288; 424/289; 424/294; 523/122; 524/288; 524/327
[58] Field of Search ................... 106/16, 17, 18, 18.32, 106/18.35, 18.36, 222, 263; 424/288, 289, 294; 523/122; 524/288, 327

[56] References Cited

U.S. PATENT DOCUMENTS 1,933,520 10/1933 Bruson .................................. 106/222
2,724,643 11/1955 Morris ................................... 424/294
3,786,152 1/1974 Minieri ............................... 106/18.32

Primary Examiner—Lorenzo B. Hayes
Attorney, Agent, or Firm—Evelyn Berlow

[57] ABSTRACT

Surface-coating compositions that have improved resistance to attack by fungi and other microorganisms contain 0.1% to 3% by weight of a biocidal compound having the structural formula

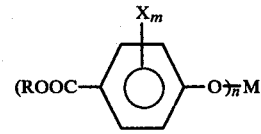

wherein each R represents an alkyl, aryl, aralkyl, alkaryl, or alicyclic group having 1 to 10 carbon atoms; X represents hydrogen, chlorine, bromine, nitro, an alkyl group having 1 to 4 carbon atoms, or an alkoxy group having 1 to 4 carbon atoms; M represents an environmentally-acceptable metal having a valence of 2, 3, or 4; m is 1 or 2; and n is the valence of the metal M.

12 Claims, No Drawings

SURFACE-COATING COMPOSITIONS CONTAINING POLYVALENT METAL SALTS OF HYDROXYBENZOIC ACID ESTERS

This invention relates to surface-coating compositions that have improved resistance to deterioration resulting from attack by bacteria, fungi, and other microorganisms. More particularly, it relates to surface-coating compositions that contain a biocidally-effective amount of a polyvalent metal salt of a p-hydroxybenzoic acid ester.

It is well known in the art that paints and varnishes often have inadequate resistance to the action of microorganisms. Some of these coating compositions, such as enamels and house paints, contain as their resinous binders drying oils, oleoresinous varnishes, or alkyd resins, which are subject to attack by fungi and bacteria. Others, for example, aqueous dispersions of water-insoluble synthetic linear polymers, generally contain as plasticizers and thickeners materials that have their origin in animal or vegetable sources and that render the compositions susceptible to mildew. The resulting deterioration of the surface-coating compositions seriously hinders their full scale utilization, particularly in those areas and in those applications that are conducive to such attack.

Various biocidal materials have been suggested for use in surface-coating compositions, but none has proven entirely satisfactory in this application. Some do not provide the required prolonged protection against attack by microorganisms, while others undergo sulfide staining and still others hydrolyze in alkaline aqueous paint systems or separate from the applied coating by migration, volatilization, or leaching after the coating has been spread in a thin layer over the surface to be protected. Some biocidal materials cause the coating compositions to gel or impart color or odor to them.

This invention relates to biocides that are of particular value in surface-coating compositions. These biocides, which are thoroughly compatible with the resinous binders that commonly are used in surface-coating compositions and which are resistant to sulfide staining, provide excellent and prolonged resistance to deterioration resulting from attack by bacteria, fungi, and other microorganisms without adversely affecting the color, pH, viscosity, and other physical properties of the surface-coating compositions.

The biocidal compounds that are used in the surface-coating compositions of this invention have the structural formula

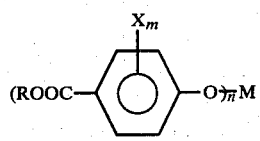

wherein the R's may be the same or different and each R represents an alkyl, aryl, aralkyl, alkaryl, or alicyclic group having 1 to 10 carbon atoms; X represents hydrogen, chlorine, bromine, nitro, an alkyl group having 1 to 4 carbon atoms, or an alkoxy group having 1 to 4 carbon atoms; M represents an environmentally-acceptable metal having a valence of 2, 3, or 4; m is 1 or 2; and n is the valence of the metal M. Among the environmentally-acceptable metals whose p-hydroxybenzoic acid ester salts can be used in the practice of this invention are zinc, copper, tin, nickel, strontium, zirconium, iron, calcium, magnesium, and antimony. The following are illustrative of these biocidal compounds:

zinc bis(ethyl p-hydroxybenzoate)
zinc bis(phenyl 3,5-diisopropyl-4-hydroxybenzoate)
cupric bis(benzyl p-hydroxybenzoate)
cupric bis(cyclopentyl 3,5-dinitro-4-hydroxybenzoate)
stannic tetrakis(isoamyl 2,6-dichloro-4-hydroxybenzoate)
nickel bis(n-octyl 2-tert.butyl-4-hydroxybenzoate)
ferric tris(methyl 2-bromo-4-hydroxybenzoate)
calcium bis(xylyl 2-ethoxy-4-hydroxybenzoate)
magnesium bis(phenyl 3,5-di-tert.butyl-4-hydroxybenzoate)
antimony tris(n-decyl 2-chloro-4-hydroxybenzoate)
strontium (methyl p-hydroxybenzoate)(isopropyl p-hydroxybenzoate)
and the like and mixtures thereof.

A preferred group of the biocidal compounds have the structural formula

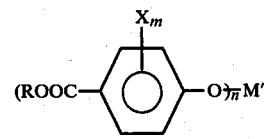

wherein M' represents zinc, copper, or tin, and R, X, m, and n have the aforementioned significance. Examples of these compounds include zinc bis(ethyl p-hydroxybenzoate)
zinc bis(phenyl 3,5-diisopropyl-4-hydroxybenzoate)
zinc bis(methyl 2-ethoxy-4-hydroxybenzoate)
cupric bis(benzyl p-hydroxybenzoate)
cupric (n-decyl 2-chloro-4-hydroxybenzoate)(isobutyl 2-chloro-4-hydroxybenzoate)
cupric bis(cyclopentyl 3,5-dinitro-4-hydroxybenzoate)
stannic tetrakis(isoamyl 2,6-dibromo-4-hydroxybenzoate)
stannic tetrakis(xylyl p-hydroxybenzoate)
stannic bis(methyl p-hydroxybenzoate)bis(propyl 2-nitro-4-hydroxybenzoate)
and the like.

Particularly valuable results have been obtained when the biocidal compound used in the surface-coating compositions had the structural formula

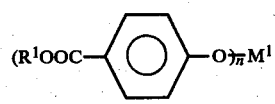

wherein the $R^1$'s may be the same or different and each $R^1$ represents an alkyl group having 1 to 5 carbon atoms or benzyl; $M^1$ represents zinc, copper, or tin; and n is the valence of the metal $M^1$. Illustrative of these biocidal compounds are the following:

zinc bis(methyl p-hydroxybenzoate)
zinc bis(propyl p-hydroxybenzoate)
zinc bis(benzyl p-hydroxybenzoate)
zinc (methyl p-hydroxybenzoate)(isobutyl p-hydroxybenzoate)
cupric bis(ethyl p-hydroxybenzoate)
cupric bis(propyl p-hydroxybenzoate)
cupric (propyl p-hydroxybenzoate)(butyl p-hydroxybenzoate)

cupric bis(benzyl p-hydroxybenzoate)
stannic tetrakis(isopropyl p-hydroxybenzoate)
stannic tetrakis(isobutyl p-hydroxybenzoate)
stannic tetrakis(benzyl p-hydroxybenzoate)
stannic bis(methyl p-hydroxybenzoate)bis(isoamyl p-hydroxybenzoate).

A single metal salt of a p-hydroxybenzoic acid ester or a mixture of two or more of these salts can be used to protect surface-coating compositions from attack by microorganisms.

The biocidal compounds of this invention may be prepared by any suitable and convenient procedure. For example, they may be prepared by contacting an aqueous suspension of one or more p-hydroxybenzoic acid esters with an aqueous solution of an alkali metal hydroxide to form a solution of the alkali metal salt of the ester and contacting this solution with a solution of a polyvalent metal compound. The polyvalent metal salt of the p-hydroxybenzoic acid ester, which is insoluble or slightly soluble in water, precipitates from the reaction mixture.

The polyvalent metal salts of this invention can be used to impart bacterial and fungal resistance to a wide variety of paints, varnishes, printing inks, and other surface-coating compositions including both water-based and organic solvent-based systems. They are particularly valuable as biocides in water-based coatings in which the resinous binder is a water-insoluble synthetic linear addition polymer.

In a preferred embodiment of the invention, the polyvalent metal salts of p-hydroxybenzoic acid esters are used as the biocide in aqueous dispersions that contain 10% to 60% by weight of a water-insoluble, film-forming, resinous binder that is a synthetic linear addition polymer, an oleoresinous binder, or a mixture of these binders. The useful aqueous dispersions of synthetic linear addition polymers are ordinarily prepared by the emulsion polymerization of ethylenically-unsaturated monomers. Illustrative of these polymers are polyvinyl acetate; polyvinyl butyrate; polyvinyl chloride; copolymers of vinyl acetate with vinyl chloride or acrylonitrile; copolymers of vinyl chloride with vinylidene chloride; polyethylene; polyisobutylene; polysytrene; copolymers of styrene with maleic anhydride or butadiene; copolymers of acrylonitrile with butadiene; copolymers of methacrylic acid esters of alcohols having 1 to 8 carbon atoms with vinyl acetate, vinyl chloride, acrylonitrile, or styrene; copolymers of acrylic acid esters of alcohols having 1 to 8 carbon atoms with vinyl acetate, vinyl chloride, acrylonitrile, or styrene; and mixtures thereof. Suitable oleoresinous binders include drying oils, such as linseed oil, tung oil, soybean oil, dehydrated castor oil, safflower oil, or fish oil; bodied drying oils; blends of drying oils or bodied drying oils with a resin component such as limed rosin, an ester gum, or phenolic resin; oleoresinous varnishes formed by heating one of the aforementioned resins with one or more drying oils or bodied drying oils; alkyd resins, which are resinous products resulting from the reaction of a polyhydric alcohol, such as pentaerythritol or glycerol, with a dicarboxylic acid, such as phthalic anhydride, and fatty acids; and mixtures thereof.

In another preferred embodiment of the invention, the metal salts of p-hydroxybenzoic acid esters are used as the biocide in organic solvent-based systems that contain an oleoresinous binder as hereinbefore defined.

Only a small concentration of the polyvalent metal salt need be present in the surface-coating compositions of this invention. The addition of as little as 0.1 percent by weight of one or more of the biocidal compounds of this invention will bring about an appreciable improvement in the resistance of the composition to attack by fungi and bacteria. Three percent or more of the biocidal compounds can be used, but these larger amounts ordinarily do not provide further improvement in the properties of the surface-coating compositions and for this reason are not usually used. The amount of the biocidal compound that will provide optimum protection for a surface-coating composition depends upon such factors as the choice of the biocidal compound, the choice of resinous binder and other ingredients of the composition and the amount of each of these materials that is used, and the application for which the coating composition is intended. In most cases 1 to 2 percent of a polyvalent metal salt of a p-hydroxybenzoic acid ester, based on the weight of the surface-coating composition, is used.

In addition to the resinous binder and the biocidal compound, the surface-coating compositions may contain various auxiliary materials, such as pigments, extenders, solvents, dyes, defoaming agents, driers, thickeners, emulsifiers, plasticizers, other biocides, and the like in the amounts ordinarily used for these purposes.

The biocidal compounds may be incorporated into the surface-coating compositions by any convenient procedure. For example, they can be added to a composition that contains the resinous binder, pigment component, and water or organic solvent. Alternatively, they can be combined with the pigments and other ingredients to form a pigment component that is mixed with the resinous binder and water or organic solvent to form the surface-coating composition.

The invention is further illustrated by the following examples. In these examples, all parts are parts by weight and all percentages are percentages by weight unless otherwise stated.

EXAMPLE 1

To a suspension of 17.5 parts (0.115 mole) of methyl p-hydroxybenzoate in 40 grams of water that had been cooled to 0°–10° C. was slowly added a 50% aqueous sodium hydroxide solution until the pH of the resulting solution was 12. A solution of 12.6 parts (0.06 mole) of zinc acetate dihydrate in 200 parts of water was added to the sodium salt solution. The white precipitate that formed was separated by filtration, washed with cold water, and dried. There was obtained 19.2 parts of zinc bis(methyl p-hydroxybenzoate).

EXAMPLE 2

To a suspension of 20.7 parts (0.155 mole) of propyl p-hydroxybenzoate in 40 parts of water that had been cooled to 0°–10° C. was slowly added a 50% aqueous sodium hydroxide solution until the pH of the resulting solution was 11.9. A solution of 12.6 parts (0.06 mole) of zinc acetate dihydrate in 200 parts of water was added to the sodium salt solution. The white precipitate that formed was separated by filtration, washed with cold water, and dried. There was obtained 23.9 parts of zinc bis(propyl p-hydroxybenzoate).

EXAMPLE 3

To a suspension of 10 parts (0.04 mole) of benzyl p-hydroxybenzoate in 10 parts of water that had been cooled to 0°-10° C. was slowly added a 50% aqueous sodium hydroxide solution until the pH of the resulting aqueous solution was 12. A solution of 5 parts (0.03 mole) of zinc sulfate in 30 parts of water was added to the sodium salt solution. The white precipitate that formed was separated by filtration, washed with cold water, and dried. There was obtained 10 parts of zinc bis(benzyl p-hydroxybenzoate).

EXAMPLE 4

To a suspension of 20.7 parts (0.115 mole) of propyl p-hydroxybenzoate in 50 parts of water that had been cooled to 0°-10° C. was slowly added a 50% aqueous sodium hydroxide solution until the pH of the resulting aqueous solution was 12. A solution of 13.9 parts (0.06 mole) of cupric nitrate trihydrate in 50 parts of water was added to the sodium salt solution. The gray-green precipitate that formed was separated by filtration, washed with cold water, and dried. There was obtained 23.3 parts of cupric bis(propyl p-hydroxybenzoate).

EXAMPLE 5

To a suspension of 20.7 parts (0.115 mole) of propyl p-hydroxybenzoate in 50 parts of water that had been cooled to 0°-10° C. was slowly added a 50% aqueous sodium hydroxide solution until the pH of the resulting solution was 12. A solution of 7.5 parts (0.03 mole) of stannic chloride in 100 parts of water was added to the sodium salt solution. The white precipitate that formed was separated by filtration, washed with cold water, and dried. There was obtained 24.5 parts of stannic tetrakis(propyl p-hydroxybenzoate).

EXAMPLE 6

A. An acrylic latex paint was prepared by grinding the following materials together in a Cowles Dissolver:

| | Parts |
|---|---|
| Water | 77.0 |
| 25% Aqueous solution of sodium salt of maleic anhydride/diisobutylene copolymer | 19.5 |
| 2,2,4-Trimethylpentane-1,3-diol monoisobutyrate | 1.5 |
| Benzyl ether of octylphenol-ethylene oxide reaction product | 2.7 |
| Defoamer | 0.9 |
| Ethylene glycol | 14.3 |
| Titanium dioxide (rutile) | 250.0 |
| Talc | 77.0 |
| Calcium carbonate | 144.0 |
| 2% Aqueous solution of hydroxyethylcellulose | 77.0 | and incorporating into the resulting blend the following materials:

| | Parts |
|---|---|
| Acrylic latex (Poly-Tex 6510) | 392.5 |
| Defoamer | 0.9 |
| Water | 19.3 |
| Ammonium hydroxide | 1.8 |
| Propylene glycol | 106.0 |

The paint had the following properties as determined by standard paint testing methods:

| | |
|---|---|
| Viscosity | 74-78 K.U. |
| Brookfield Viscosity (No. 3 spindle, 60 rpm) | 1600 cps. |

To portions of this paint were added 2% by weight of the biocidal compounds of this invention.

B. An oil-based paint was prepared by mixing together the following materials:

| | Parts |
|---|---|
| Titanium Dioxide | 225.0 |
| Talc | 400.0 |
| Long oil alkyld resin (Aroplaz 1266M-60) | 420.0 |
| Mineral spirits | 167.0 |
| Calcium drier (4% Ca) | 12.0 |
| Zinc Drier (8% Zn) | 5.0 |
| Cobalt drier (6% Co) | 1.6 |

To portions of this paint were added 2% by weight of the biocidal compounds of this invention.

EXAMPLE 7

Samples of the acrylic latex paint and the oil-based paint whose preparation was described in Example 6 were evaluated by the following procedure: Pieces of drawdown paper were brush-coated with the paint. The painted strips were air dried for one day and then leached with water in one gallon containers at a flow rate of 6 changes per day. The strips were then dried and cut into 3 cm. squares. Non-leached samples were prepared by brush-coating strips of drawdown paper with the paint, air drying the painted strips for one day, and then cutting them into 3 cm. squares.

The coated paper squares were placed on the surface of solidified malt agar. The paint films were then inoculated with either a suspension of spores of the fungi *Aspergillus niger, Penicillium funiculosum,* and *Gliocladium virens* (Trichoderma) or a suspension of spores of *Aureobasidium pullulans.* The plates were incubated at 30° C. under 85-95% relative humidity for four weeks. The surface of the samples was examined weekly and the fungal growth rated on a scale of zero to 10, with a rating of zero indicating no growth of fungus on the sample and a rating of 10 indicating complete surface coverage.

The biocidal compounds tested and the results obtained are set forth in Tables I and II.

TABLE I

Activity of Metal Salts of p-Hydroxybenzoic Acid Esters as Biocides in an Acrylic Latex Paint

| | Biocide | | | |
|---|---|---|---|---|
| | Product of Ex. 2 | Product of Ex. 4 | Product of Ex. 5 | None |
| Growth Rating: *Aureobasidium pullulans* Non-leached | | | | |
| 1 Week | 0 | 0 | 1 | 10 |
| 2 Weeks | 1 | 2 | 3 | 10 |
| 3 Weeks | 1 | 3 | 5 | 10 |
| 4 Weeks | 1 | 3 | 5 | 10 |
| Leached | | | | |
| 1 Week | 1 | 0 | 5 | 10 |
| 2 Weeks | 4 | 4 | 8 | 10 |
| 3 Weeks | 6 | 6 | 8 | 10 |
| 4 Weeks | 6 | 10 | 8 | 10 |
| Growth Rating: *Aspergillus niger, Penicillium funiculosum,* and *Gliocladium virens* | | | | |

TABLE I-continued
Activity of Metal Salts of p-Hydroxybenzoic Acid Esters as Biocides in an Acrylic Latex Paint

| | Biocide | | | |
|---|---|---|---|---|
| | Product of Ex. 2 | Product of Ex. 4 | Product of Ex. 5 | None |
| (Trichoderma) | | | | |
| Non-leached | | | | |
| 1 Week | 1 | 1 | 1 | 10 |
| 2 Weeks | 3 | 3 | 1 | 10 |
| 3 Weeks | 6 | 6 | 3 | 10 |
| 4 Weeks | 10 | 8 | 8 | 10 |
| Leached | | | | |
| 1 Week | 2 | 1 | 3 | 10 |
| 2 Weeks | 8 | 5 | 9 | 10 |

TABLE II
Activity of Metal Salts of p-Hydroxybenzoic Acid Esters as Biocides in Oil-based Paint

| | Biocide | | |
|---|---|---|---|
| | Product of Ex. 2 | Product of Ex. 5 | None |
| Growth Rating: *Aureobasidium pullulans* | | | |
| Non-leached | | | |
| 1 Week | 1 | 1 | 2 |
| 2 Weeks | 2 | 1 | 5 |
| 3 Weeks | 2 | 3 | 8 |
| 4 Weeks | 3 | 5 | 10 |
| Leached | | | |
| 1 Weeks | 1 | 1 | 2 |
| 2 Weeks | 4 | 2 | 5 |
| 3 Weeks | 5 | 5 | 8 |
| 4 Weeks | 5 | 8 | 10 |
| Growth Rating: *Aspergillus niger, Penicillium funiculosum,* and *Gliocladium virens* (Trichoderma) | | | |
| Non-leached | | | |
| 1 Week | 0 | 1 | 2 |
| 2 Weeks | 1 | 1 | 3 |
| 3 Weeks | 1 | 3 | 5 |
| 4 Weeks | 2 | 4 | 8 |
| Leached | | | |
| 1 Week | 1 | 1 | 2 |
| 2 Weeks | 1 | 4 | 5 |
| 3 Weeks | 1 | 5 | 8 |
| 4 Weeks | 2 | 9 | 10 |

What is claimed is:

1. A surface-coating composition having improved resistance to attack by fungi and other microorganisms that comprises
   (a) a water-insoluble resinous binder selected from the group consisting of synthetic linear addition polymers prepared by the emulsion polymerization of ethylenically-unsaturated monomers, oleoresinous binders, and mixtures thereof and
   (b) 0.1% to 3%, based on the weight of the composition, of a biocidal compound having the structural formula

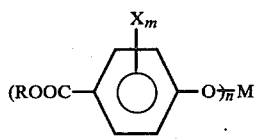

wherein the R's may be the same or different and each R represents an alkyl, aryl, aralkyl, alkaryl, or alicyclic group having 1 to 10 carbon atoms; X represents hydrogen, chlorine, bromine, nitro, an alkyl group having 1 to 4 carbon atoms, or an alkoxy group having 1 to 4 carbon atoms, M represents an environmentally-acceptable metal having a valence of 2, 3, or 4; m is 1 or 2; and n is the valence of the metal M.

2. A surface-coating composition as set forth in claim 1 that contains 1% to 2%, based on the weight of the composition, of said biocidal compound.

3. A surface-coating composition as set forth in claim 1 wherein the biocidal compound has the structural formula

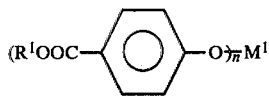

wherein the $R^1$'s may be the same or different and each $R^1$ represents an alkyl group having 1 to 5 carbon atoms or benzyl; $M^1$ represents a polyvalent metal selected from the group consisting of zinc, copper, and tin; and n is the valence of the metal $M^1$.

4. A surface-coating composition as set forth in claim 3 wherein the biocidal compound is zinc bis(propyl p-hydroxybenzoate).

5. A surface-coating composition as set forth in claim 3 wherein the biocidal compound is cupric bis(propyl p-hydroxybenzoate).

6. A surface-coating composition as set forth in claim 3 wherein the biocidal compound is stannic tetrakis(propyl p-hydroxybenzoate).

7. The method of controlling the growth of fungi and other microorganisms in a surface-coating composition that contains a water-insoluble resinous binder selected from the group consisting of synthetic linear addition polymers prepared by the emulsion polymerization of ethylenically-unsaturated monomers, oleoresinous binders, and mixtures thereof that comprises incorporating in said composition 0.1% to 3%, based on the weight of said composition, of a biocidal compound having the structural formula

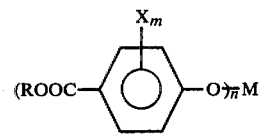

wherein the R's may be the same or different and each R represents an alkyl, aryl, aralkyl, alkaryl, or alicyclic group having 1 to 10 carbon atoms; X represents hydrogen, chlorine, bromine, nitro, an alkyl group having 1 to 4 carbon atoms, or an alkoxy group having 1 to 4 carbon atoms; M represents an environmentally-acceptable metal having a valence of 2, 3, or 4; m is 1 or 2; and n is the valence of the metal M.

8. The method of claim 7 wherein 1% to 2%, based on the weight of the composition, of the biocidal compound is incorporated into the composition.

9. The method of claim 7 wherein the biocidal compound has the structural formula

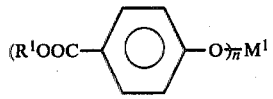

wherein the $R^1$'s may be the same or different and each $R^1$ represents an alkyl group having 1 to 5 carbon atoms or benzyl; $M^1$ represents a polyvalent metal selected from the group consisting of zinc, copper, and tin; and n is the valence of the metal $M^1$.

10. The method of claim 9 wherein the biocidal compound is zinc bis(propyl p-hydroxybenzoate).

11. The method of claim 9 wherein the biocidal compound is cupric bis(propyl p-hydroxybenzoate).

12. The method of claim 9 wherein the biocidal compound is stannic tetrakis(propyl p-hydroxybenzoate).

* * * * *